US006884617B1

(12) United States Patent
Robb et al.

(10) Patent No.: US 6,884,617 B1
(45) Date of Patent: Apr. 26, 2005

(54) ISOLATED NUCLEIC ACID ENCODING MURINE MUSCULIN

(75) Inventors: Lorraine Robb, North Melbourne (AU); Glenn C. Begley, Westlake Village, CA (US); Richard P. Harvey, Kingsford (AU)

(73) Assignee: Walter and Eliza Hall Institute of Medical Research (AU)

( * ) Notice: Subject to any disclaimer, the term of this patent is extended or adjusted under 35 U.S.C. 154(b) by 0 days.

(21) Appl. No.: 09/744,778

(22) PCT Filed: Jul. 30, 1999

(86) PCT No.: PCT/AU99/00623

§ 371 (c)(1),
(2), (4) Date: Jun. 28, 2001

(87) PCT Pub. No.: WO00/06720

PCT Pub. Date: Feb. 10, 2000

(30) Foreign Application Priority Data

Jul. 30, 1998 (AU) .............................................. PP4955

(51) Int. Cl.$^7$ ......................... C12N 15/63; C12N 15/12; C12N 15/70; C12N 15/74; C12N 15/79

(52) U.S. Cl. .................................... 435/320.1; 536/23.5

(58) Field of Search ....................... 536/23.5; 435/320.1

(56) References Cited

U.S. PATENT DOCUMENTS 5,795,723 A    8/1998  Tapscott et al.
5,885,797 A  * 3/1999  Chen et al. ................. 435/69.1

FOREIGN PATENT DOCUMENTS

WO    WO 97/16548    5/1997
WO    WO 98/13491    4/1998
WO    WO 98/27206    6/1998

OTHER PUBLICATIONS

Massari, et al. (1998) "Characterization of ABF–1, a Novel Basic Helix–Loop–Helix Transcription Factor Expressed in Activated B Lymphocytes" Mol. and Cell. Bio. 18:3130–3139.
Robb, et al. (1998) "Musculin: a Murine Basic Helix–Loop–Helix Transcription Factor Gene Expressed in Embryonic Skeletal Muscle" Mechanisms of Dev. 76:197–201.
Akazawa et al. (1995) "A Mammalian Helix–Loop–Helix Factor Structurally Related to the Product of Drosophila Proneural Gene atonal Is a Positive Transscriptional Regulator Expressed in the Developing Nervous System" J. Biol. Chem. 270(15): 8730–8738.
Begley et al. (1992) "Molecular Characterization of NSCL, a Gene Encoding a Helix–Loop–Helix Protein Expressed in the Developing Nervous Systems" Proc. Natl. Acad. Sci. USA 89:38–42.

Burgess et al. (1995) "Paraxis: A Basic Helix–Loop–Helix Protein Expressed In Paraxial Mesoderm and Developing Somites" Dev. Biol. 168: 296–306.
Cserjesi et al. (1995) "Scleraxis: a Basic Helix–Loop–Helix Protein that Prefigures Skeletal Formation During Mouse Embryogenesis" Development 121: 1099–1110.
Davis et al. (1987) "Expression of a Single Transfected cDNA Converts Fibroblasts to Myoblasts" Cell 51: 987–1000.
Edmondson et al. (1989) "A gene with homology to the myc similarity region of MyoD1 is expressed during myogenesis and is sufficient to activate the muscle differentiation program" Genes & Development 3:628–640.
Georgia et al. (1997) "A Basic–Helix–Loop–Helix Protein Expressed in Precursors of Drosophla Longitudinal Visceral Muscles" Mech. Devel. 69: 115–124.
Jan et al. (1993) "HLH Proteins, Fly Neurogenesis, and Vrtebrate Myogenesis" Cell 75:827–830.
Lyons et al. (1995) "Myogenic and Morphogenetic Defects In the Heart Tubes of Murine Embryos Lacking the Homeo Box Gene Nkx2–5" Genes and Development 9:1654–1666.
Molkentin et al. (1995) "A Calcineurin–Dependent Transcriptional Pathway for Cardiac/Hypertrophy" Cell 93: 215–228.
Murre et al. (1994) "Structure and Function of Helix–Loop–Helix Proteins" Biochimica et Biophysica Acta 1218: 125–135.
Murre et al. (1989) "A New DNA Binding and Dimerizaton Motif In Immunoglobulin Enhance Binding, Daughterless, MyoD, and myc Proteins" Cell 56: 777–793.
Robb et al. (1996) "Structural Analysis of the Gene Encoding the Murine Interleukin–11 Receptor α–Chain and a Related Locus" J. Biol. Chem. 271 (23): 13754–13761.
Robb et al. (1998) "Infertility in Female Mice Lacking the Receptor for Interleukin 11 is Due to a Defective Uterne Response to Implantation" Nature Medicine 4(3):303–307.
Srivastava et al. (1995) "A Subclass of bHLH Proteins Required for Cardiac Morphogenesis" Science 270: 1995–1999.
Tajbakhsh et al. (1998) "Somite Development: Constructing the Vertebrate Body" Cell 92: 9–16.

(Continued)

Primary Examiner—Terry McKelvey
(74) Attorney, Agent, or Firm—Duane Morris LLP

(57) ABSTRACT

The present invention relates generally to a regulatory molecule and to genetic sequences encoding same. More particularly, the present invention provides a molecule involved in, associated with or which otherwise facilitates myogenesis. In a particularly preferred embodiment, the regulatory molecule is a transcription factor involved in the expression of genes resulting in the determination of skeletal muscle (a sequence encoding the regulatory molecule is disclosed within the specification as Seq. Id. No: 2). The identification of the regulatory molecule of the present invention permits the development of agents capable of modulating myogenesis including therapeutic agents capable of ameliorating aberrations in pyogenesis such as but not limited to myogenic cancers.

5 Claims, 9 Drawing Sheets

OTHER PUBLICATIONS

Voronova et al. (1990) "Mutations that disrupt DNA binding and dimer formation in the E47 helix–loop–helix protein map to distinct domains" Proc. Natl. Acad. Sci. USA 87: 4722–4726.

Wolf et al. (1991) "The M–Twist Gene of Mus is Expressed in Subsets of Mesodermal Cells and Is Closely Related to the Xenopus X–twi and the *Drosophila* twist Genes" Developmental Biology 143:363–373.

* cited by examiner

```
aagttcagca gagccctggg ctacagggtc agcagcagat cgcgcccact       50
ccaggcgccc agctcacagg ggagcctcag tgcggaggca agccctggtc      100
tctggtcctc ccctgggctc tcccacaccc catcctctgt cagagagaag      150
aagccagaga aagcgagact ggccggggag gagaaaggcg ggcgcgcgtg      200
ggcgcccggg aataggcg atg tcc acc ggc tcg gtg agt gac ccc    245
                   Met Ser Thr Gly Ser Val Ser Asp Pro
                    1               5 gaa gac tcg gag atg agg ggg ctg cag agg gtc tac ccg gcc    287
Glu Asp Ser Glu Met Arg Gly Leu Gln Arg Val Tyr Pro Ala
 10                  15                  20 ccg gcc tcc aag agg ccg ccc ctg ctc cgc atg gag cgc ggt    329
Pro Ala Ser Lys Arg Pro Pro Leu Leu Arg Met Glu Arg Gly
             25                  30                  35
```

FIGURE 1A (i)

```
tac ggc tcg ccc agc gac att tct tct gcg gaa gag gag gac    371
Tyr Gly Ser Pro Ser Asp Ile Ser Ser Ala Glu Glu Glu Asp
 40                      45                      50 ggt gaa gag gag ccc ggc tcc ctg gga gcc gcg gga gga tgc    413
Gly Glu Glu Glu Pro Gly Ser Leu Gly Ala Ala Gly Gly Cys
             55                      60                 65 aag agg aag cgg ctc cgt ggg gct gac gct ggc gca ggt        455
Lys Arg Lys Arg Leu Arg Gly Ala Asp Ala Gly Ala Gly
                     70                      75 ggc cgc gca ggc ggt gcg ggg aaa aag ccg ctc ccg cct aag    497
Gly Arg Ala Gly Gly Ala Gly Lys Lys Pro Leu Pro Pro Lys
 80                      85                      90
```

FIGURE 1A (ii)

```
ggc tcg gcc gca gag tgc aag cag tcg cag cgg aat gcg gcc    539
Gly Ser Ala Ala Glu Cys Lys Gln Ser Gln Arg Asn Ala Ala
         95                 100                105 aac gcc cgc gaa cgc gcc cgg atg cgc gtg ctg agc aaa gcc    581
Asn Ala Arg Glu Arg Ala Arg Met Arg Val Leu Ser Lys Ala
                110                 115                120 ttc tcc aga ctg aag acc agc ctg ccc tgg gtg ccg ccc gac    623
Phe Ser Arg Leu Lys Thr Ser Leu Pro Trp Val Pro Pro Asp
        125                 130                 135 acc aag ctt tcc aaa ctg gac acg ctg cgc ctg gct tcc agc    665
Thr Lys Leu Ser Lys Leu Asp Thr Leu Arg Leu Ala Ser Ser
                140                 145
```

FIGURE 1A (iii)

```
tac atc gcg cac ctg cgc cag ctg ctg cag gag gac cgc tac     707
Tyr Ile Ala His Leu Arg Gln Leu Leu Gln Glu Asp Arg Tyr
        150                 155                 160 gag gac agc tat gtg cac cct gtg aac ctg acg tgg cca ttc     749
Glu Asp Ser Tyr Val His Pro Val Asn Leu Thr Trp Pro Phe
        165                 170                 175 gtg gtc tct gga cgc cca gac tct gac agc aaa gac gtt tct     791
Val Val Ser Gly Arg Pro Asp Ser Asp Ser Lys Asp Val Ser
        180                 185                 190 gca gcc aac agg ctt tgt gga act tcc gct tagagggaca          831
Ala Ala Asn Arg Leu Cys Gly Thr Ser Ala
        195                 200
```

FIGURE 1A (iv)

| | | | | |
|---|---|---|---|---|
| ggacagttag | atggattgtg | gtaaacgcaa | aggactgggc | caaggaagtc | 881
| ccactggatt | ctggaccttc | tcctttccct | gggcctgtga | acaagacagg | 931
| agacaagtgt | tgtttgccct | cctggagcgc | aggtggccat | gggtgcccca | 981
| aatcagtgca | aacttctgta | accaaagaaa | gcccagtttc | aggggaagaa | 1031
| tacgtggacc | aggtaaaaac | ctagggcttt | agctctgatc | acaaccccct | 1081
| gcctgctatc | tgagtccagt | gcagaaacgg | gttggttttg | aagctaatct | 1131
| tgattgcctt | gtggttgatg | gcaaggtcct | gcacagccag | gtccttctgt | 1181
| gaccgtggat | gagagctgtt | tcccagcact | agaaagaagg | ccggcattag | 1231
| agctcttcgg | gggcctgtca | ctaagggcag | tgttgctaca | gacagtggca | 1281
| tactcttcct | gggcaggaca | tgttgagatg | gagacattaa | ctccaggtgc | 1331
| tggttttgct | cgaaatctct | gcagactggg | gttcatttcc | tgagttccct | 1381
| cctctgttta | atcagtgttg | ggtctccatt | cagtgagtgc | agcttgttta | 1431
| tggggtctca | gctccttccc | acccacactg | tcccctattt | gggacatgt | 1481
| gcttcacccc | tctaattgtc | tcaccctgcc | acagcatagc | ctttctgtggg | 1531
| gttcctggtc | tttcagggat | gtactattct | tcctggtcca | aggactgtgt | 1581

FIGURE 1A (v)

```
gtggtgggtg gctggggcta gggctggtct ctattatact ggtttctacc    1631
cagtacatgg tgcttactgg tcctggcaat gctgcactat catggtaact    1681
aacatatgta ttttttatgg acaaaaa                             1718
```

ISOLATED NUCLEIC ACID ENCODING MURINE MUSCULIN

FIELD OF THE INVENTION

The present invention relates generally to a regulatory molecule and to genetic sequences encoding same. More particularly, the present invention provides a molecule involved in, associated with or which otherwise facilitates myogenesis. In a particularly preferred embodiment, the regulatory molecule is a transcription factor involved in the expression of genes resulting in the determination of skeletal muscle. The identification of the regulatory molecule of the present invention permits the development of agents capable of modulating myogenesis including therapeutic agents capable of ameliorating aberrations in myogenesis such as but not limited to myogenic cancers.

BACKGROUND OF THE INVENTION

Bibliographic details of the publications numerically referred to in this specification are collected at the end of the description.

The exploitation of recombinant DNA technology in the treatment and prophylaxis of disease conditions requires a level of understanding of regulatory mechanisms involved in gene expression commensurate with the complexity of the genetic disorder to be treated. This is particularly the case for the myriad of regulatory molecules involved in cell fate determination and tissue differentiation during developmental processes.

One important class of regulatory molecules are members of the basic helix-loop-helix (bHLH) family of transcription factor proteins which are involved in cellular proliferation and differentiation during developmental processes including haemopoiesis, myogenesis and neurogenesis (1, 2). These proteins share a common sequence motif consisting of a basic (b) region and an adjacent helix-loop-helix (HLH) structure. The b region is important for DNA binding while the HLH domain mediates dimerization (3, 4).

Myogenic-specific bHLH proteins are involved in the activation of genes required for proper vertebrate development. bHLH proteins MyoD, Myf-5, Myf-4 and myogenin interact with class I HLH proteins.

bHLH proteins are also involved in antigen dependent B-cell differentiation. ABF-1 is a bHLH protein capable of binding with the product of the E2A gene to the E2 box elements of the b region of ABF-1.

In work leading up to the present invention, the inventors sought to identify other bHLH genes. The inventors have identified a gene having nucleotide sequence similarity to ABF-1 but which is involved in myogenesis.

SUMMARY OF THE INVENTION

Throughout this specification, unless the context requires otherwise, the word "comprise", or variations such as "comprises" or "comprising", will be understood to imply the inclusion of a stated element or integer or group of elements or integers but not the exclusion of any other element or integer or group of elements or integers.

The subject specification contains nucleotide and amino acid sequence information prepared using the programme PatentIn Version 2.0, presented herein after the bibliography. Each nucleotide or amino acid sequence is identified in the sequence listing by the numeric indicator <210>followed by the sequence identifier (e.g. <210>1, <210>2, etc). The length, type of sequence (DNA, protein (PRT), etc) and source organism for each nucleotide or amino acid sequence are indicated by information provided in the numeric indicator fields <211>, <212>and <213>, respectively. Nucleotide and amino acid sequences referred to in the specification are defined by the information provided in numeric indicator field <400> followed by the sequence identifier (eg. <400>1, <400>2, etc).

One aspect of the present invention provides an isolated nucleic acid molecule encoding a regulatory protein involved in, associated with or which otherwise facilitates the activation of genes involved in myogenesis, said regulatory protein lacking the alanine-threonine myogenic recognition motif.

Another aspect of the present invention contemplates an isolated nucleic acid molecule comprising a sequence of nucleotides encoding or a complementary sequence of nucleotides encoding the amino acid sequence substantially as set forth in <400>2 (SEQ ID NO: 2) or an amino acid sequence having at least 60% identity thereto, wherein said nucleic acid molecule encodes a protein involved in, associated with or which otherwise facilitates the activation of genes involved in myogenesis but which lacks the alanine-threonine myogenic recognition motif.

Still another aspect of the present invention is directed to an isolated nucleic acid molecule comprising a sequence of nucleotides or a complementary sequence of nucleotides substantially as set forth in <400>1 (SEQ ID NO: 1) or a sequence having at least 60% identity thereto or which is capable of hybridizing to <400>1 (SEQ ID NO: 1) under low stringency conditions at 42° C., wherein said nucleic acid molecule encodes a protein involved in, associated with or which otherwise facilitates the activation of genes involved in myogenesis but which lacks the alanine-threonine myogenic recognition motif.

Yet another aspect of the present invention contemplates an isolated protein or a functional derivative thereof comprising a sequence of amino acids substantially as set forth in <400>2 (SEQ ID NO: 2) or an amino acid sequence having at least about 60% similarity to <400>2 (SEQ ID NO: 2) wherein said protein is involved in, associated with or which otherwise facilitates activation of genes involved with myogenesis and lacks the alnine-threonine myogenic recognition motif found in the myogenic regulatory factors myoD, mrf-4, mrf-5 and myogenin (25).

The nucleic acid of the present invention is referred to herein as "musculin". The product of the musculin gene is "musculin".

DETAIL DESCRIPTION OF THE PREFERRED EMBODIMENTS

Figure 1C:
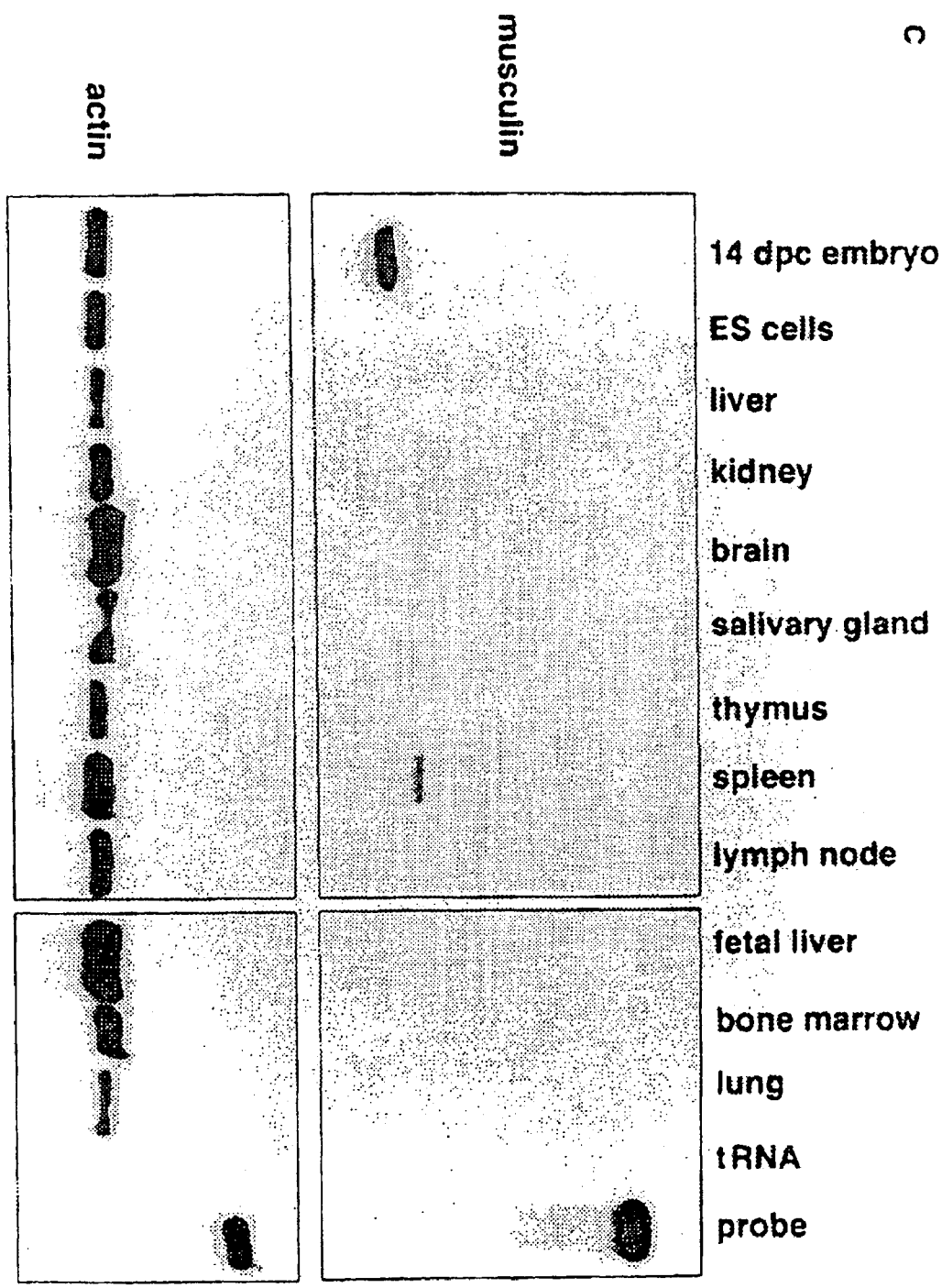
FIG. 1 is a representation of (A) nucleotide sequence (<400>1) (SEQ ID NO: 1) and deduced amino acid sequence (<400>2) (SEQ ID NO: 2) of murine musculin. (B) Comparison of the predicted musculin bHLH amino acid sequence with selected bHLH factors. Amino acid identities are shown as white on black. The myogenic (AT) recognition motif is shaded. References for the protein sequences are as follows: [6, 7, 12–18]. (C) Rnase protection analysis of adult murine tissues with a musculin riboprobe (nt 306–524). Probe, full length probe; t-RNA, probe after Rnase digestion; ES cells, embryonic stem cells.

The present invention is predicated in part on the identification of a regulatory gene termed "musculin"involved in myogenesis.

Reference herein to "musculin" includes reference to all mammalian functional homologues as well as all derivatives thereof.

Accordingly, one aspect of the present invention provides an isolated nucleic acid molecule encoding a regulatory protein involved in, associated with or which otherwise facilitates the activation of genes involved in myogenesis, said regulatory protein lacking the alanine-threonine myogenic recognition motif.

The term "protein" includes a polypeptide or peptide.

Preferably, the nucleic acid molecule, musculin, encodes the amino acid sequence set forth in <400>2 (SEQ ID NO: 2).

Accordingly, another aspect of the present invention is directed to an isolated nucleic acid molecule comprising a sequence of nucleotides encoding or a complementary sequence of nucleotides encoding the amino acid sequence substantially as set forth in <400>2 (SEQ ID NO: 2) or an amino acid sequence having at least 60% identity thereto, wherein said nucleic acid molecule encodes a protein involved in, associated with or which otherwise facilitates the activation of genes involved in myogenesis but which lacks the alanine-threonine myogenic recognition motif.

More particularly, the present invention contemplates an isolated nucleic acid molecule comprising a sequence of nucleotides or a complementary sequence of nucleotides substantially as set forth in <400>1 (SEQ ID NO: 1) or a sequence having at least 60% identity thereto or which is capable of hybridizing to <400>1 (SEQ ID NO: 1) under low stringency conditions at 42° C., wherein said nucleic acid molecule encodes a protein involved in, associated with or which otherwise facilitates the activation of genes involved in myogenesis but which lacks the alanine-threonine myogenic recognition motif.

The musculin may be in DNA (e.g. cDNA or genomic DNA), RNA (e.g. mRNA) or hybrid DNA:RNA form. The nucleic acid molecule of the present invention does not correspond to ABF-1 and is not a functional homologue of ABF-1 notwithstanding their structural homology.

In a particularly preferred embodiment, the present invention provides an isolated protein or a function derivative thereof comprising a sequence of amino acids substantially as set forth in <400>2 (SEQ ID NO: 2) or an amino acid sequence having at least about 60% similarity to <400>2 (SEQ ID NO: 2) wherein said protein is involved in, associated with or which otherwise facilitates activation of genes involved with myogenesis and lacks the alanine-threonine myogenic recognition motif.

The term "identity" is used in its broadest sense to include the number of exact nucleotide or amino acid matches having regard to an appropriate alignment using a standard algorithm, such as but not limited to the Geneworks program (Intelligenetics).

The nucleotide sequence of <400>1 (SEQ ID NO: 1) corresponds to musculin. The amino acid sequence of <400>2 (SEQ ID NO: 2) corresponds to musculin.

Reference herein to a low stringency at 42° C. includes and encompasses from at least about 1% v/v to at least about 15% v/v formamide and from at least about 1M to at least about 2M salt for hybridisation, and at least about 1M to at least about 2M salt for washing conditions. Alternative stringency conditions may be applied where necessary, such as medium stringency, which includes and encompasses from at least about 16% v/v to at least about 30% v/v formamide and from at least about 0.5M to at least about 0.9M salt for hybridisation, and at least about 0.5M to at least about 0.9M salt for washing conditions, or high stringency, which includes and encompasses from at least about 31% v/v to at least about 50% v/v formamide and from at least about 0.01M to at least about 0.15M salt for hybridisation, and at least about 0.01M to at least about 0.15M salt for washing conditions. In general, washing is carried out at $T_m=69.3+0.41$ (G+C) % [19]=–12° C. However, the $T_m$ of a duplex DNA decreases by 1° C. with every increase of 1% in the number of mismatched based pairs (20).

Although the musculin of the present invention is exemplified in relation to the gene in murine species, the present invention extends to functional homologues in human and other non-human animals such as in primates, laboratory test animals (e.g. rates, rabbits, guinea pigs, hamsters), companion animals (e.g. dogs, cats), livestock animals (e.g. sheep, pigs, horses, donkeys, cows) and captive wild animals (e.g. deer, fox).

The present invention further extends to single or multiple nucleotide substitutions, deletions and/or additions to the nucleotide sequence set forth in <400>1 (SEQ ID NO: 1). Such substitutions, deletions and/or additions of nucleotides defining musculin are encompassed by the term "derivatives" which covers mutants, fragments, parts and segments of the musculin nucleotide sequence.

A derivative of the musculin of the present invention also includes nucleic acid molecules capable of hybridizing to the nucleotide sequence set forth in <400>1 (SEQ ID NO: 1) under low stringency conditions at 42° C. The present invention extends to alternative levels of stringency such as medium and high.

The derivatives of the nucleic acid molecule of the present invention include oligonucleotides, PCR primers, antisense molecules, molecules suitable for use in co-suppression and fusion nucleic acid molecules. Ribozymes are also contemplated by the present invention directed to musculin.

The nucleic acid molecules of the present invention may be ligated to an expression vector capable of expression in a prokaryotic cell (e.g. *E coli*) or a eukaryotic cell (e.g. yeast cells, fungal cells, insect cells, mammalian cells or plant cells).

In accordance with the present invention, it is proposed that mutations in musculin cause, facilitate or contribute to aberrations in muscle development. The cloning of this gene now provides a means for genetic screening for myogenic disease conditions. Myogenic disease conditions include but are not limited to myopathies and muscular dystrophies such as hereditary, inflammatory, endocrine, metabolic and toxic disorders. Myogenic disease conditions also extend to neuromuscular and skeletomuscular disorders.

Genetic screening may be conducted by determining full expression or full-length transcript production by Northern blot, cloning and sequencing of the musculin or identifying mutations by oligonucleotide hybridization or by direct sequencing of PCR products of the musculin. In addition, the present invention extends to nucleic acid molecules having translation-terminating mutations leading to truncation mutants. The detection of truncation mutants may be important for genetic analysis of people with myogenic disease conditions or with a propensity to develop myogenic disease conditions, determined on, for example, hereditary grounds. Truncated musculin translation products may also be useful in developing therapeutic agents such as antagonists or for developing antibodies. Truncational mutants may be readily detected by a direct protein truncation test. See for example Van der Luut et al (11). In essence, DNA fragments including PCR products or corresponding mRNA molecules are subjected to in vitro translation and optionally also transcription and the translation products assayed by, for example, SDS-PAGE or by differential antibody binding assays. This assay may also be employed to screen for agents capable of inducing truncation mutations or for acting as antagonists for truncation mutant-inducing agents.

Alternatively, the expression product of musculin (i.e. musculin), may be assayed by, for example, antibody screening such as in an ELISA.

Accordingly, another aspect of the present invention provides a proteinaceous molecule having an amino acid sequence substantially as set forth in <400>2 (SEQ D NO: 2) or having at least about 60% identity thereto. The amino acid sequence of <400>2 (SEQ ID NO: 2) corresponds to musculin. The present invention also encompasses derivatives of musculin such as amino acid substitutions, deletions and/or additions to the musculin amino acid sequence. Particularly important derivates include antigenic fragments and analogues useful in immunoassays and as therapeutic agents as well as other fragments carrying B cell and/or T cell linear conformational epitopes. "Additions" to the amino acid sequence include fusion with peptides, polypeptides and proteins.

Analogues of musculin contemplated herein include, but are not limited to, modification to side chains, incorporating of unnatural amino acids and/or their derivatives during peptide, polypeptide or protein synthesis and the use of crosslinkers and other methods which impose conformational constraints on the proteinaceous molecule or their analogues. Such chemical analogues may be useful in providing stable means for diagnostic purposes or for producing agonists or antagonists or for producing stable molecules for use in natural product screening.

Examples of side chain modifications contemplated by the present invention include modifications of amino groups such as by reductive alkylation by reaction with an aldehyde followed by reduction with NaBH$_4$; amidination with methylacetimidate; acylation with acetic anhydride; carbamoylation of amino groups with cyanate; trinitrobenzylation of amino groups with 2,4,6-trinitrobenzene sulphonic acid (TNBS); acylation of amino groups with succinic anhydride and tetrahydrophthalic anhydride; and pyridoxylation of lysine with pyridoxal-5-phosphate followed by reduction with NaBH$_4$.

The guanidine group of arginine residues may be modified by the formation of heterocyclic condensation products with reagents such as 2,3-butanedione, phenylglyoxal and glyoxal. The carboxyl group may be modified by carbodiimide activation via O-acylisourea formation followed by subsequent derivitisation, for example, to a corresponding amide.

Sulphydryl groups may be modified by methods such as carboxymethylation with iodoacetic acid or iodoacetamide; performic acid oxidation to cysteic acid; formation of a mixed disulphides with other thiol compounds; reaction with maleimide, maleic anhydride or other substituted maleimide; formation of mercurial derivatives using 4-chloromercuribenzoate, 4-chloromercuriphenylsulphonic acid, phenylmercury chloride, 2-chloromercuri-4-nitrophenol and other mercurials; carbamoylation with cyanate at alkaline pH.

Tryptophan residues may be modified by, for example, oxidation with N-bromosuccinimide or alkylation of the indole ring with 2-hydroxy-5-nitrobenzyl bromide or sulphenyl halides.

Tyrosine residues on the other hand, may be altered by nitration with tetranitromethane to form a 3-nitrotyrosine derivative.

Modification of the imidazole ring of a histidine residue may be accomplished by alkylation with iodoacetic acid derivatives or N-carbethoxylation with diethylpyrocarbonate.

Examples of incorporating unnatural amino acids and derivatives during peptide synthesis include, but are not limited to, use of norleucine, 4-amino butyric acid, 4-amino-3-hydroxy-5-phenylpentanoic acid, 6-aminohexanoic acid, t-butylglycine, norvaline, phenylglycine, ornithine, sarcosine, 4-amino-3-hydroxy-6-methylheptanoic acid, 2-thienyl alanine and/or D-isomers of amino acids. A list of unnatural amino acids, contemplated herein is shown in Table 1.

TABLE 1

| Non-conventional amino acid | Code |
|---|---|
| α-aminobutyric acid | Abu |
| α-amino-α-methylbutyrate | Mgabu |
| aminocyclopropane-carboxylate | Cpro |
| aminoisobutyric acid | Aib |
| aminonorbornyl-carboxylate | Norb |
| cyclohexylalanine | |
| cyclopentylalanine | Cpen |
| D-alanine | Dal |
| D-arginine | Darg |
| D-aspartic acid | Dasp |
| D-cysteine | Dcys |
| D-glutamine | Dgln |
| D-glutamic acid | Dglu |
| D-histidine | Dhis |
| D-isoleucine | Dile |
| D-leucine | Dleu |
| D-lysine | Dlys |
| D-methionine | Dmet |
| D-ornithine | Dorn |
| D-phenylalanine | Dphe |
| D-proline | Dpro |

TABLE 1-continued

| Non-conventional amino acid | Code |
|---|---|
| D-serine | Dser |
| D-threonine | Dthr |
| D-tryptophan | Dtrp |
| D-tyrosine | Dtyr |
| D-valine | Dval |
| D-α-methylalanine | Dmala |
| D-α-methylarginine | Dmarg |
| D-α-methylasparagine | Dmasn |
| D-α-methylaspartate | Dmasp |
| D-α-methylcysteine | Dmcys |
| D-α-methylglutamine | Dmgln |
| D-α-methylhistidine | Dmhis |
| D-α-methylisoleucine | Dmile |
| D-α-methylleucine | Dmleu |
| D-α-methyllysine | Dmlys |
| D-α-methylmethionine | Dmmet |
| D-α-methylornithine | Dmorn |
| D-α-methylphenylalanine | Dmphe |
| D-α-methylproline | Dmpro |
| D-α-methylserine | Dmser |
| D-α-methylthreonine | Dmthr |
| D-α-methyltryptophan | Dmtrp |
| D-α-methyltyrosine | Dmty |
| D-α-methylvaline | Dmval |
| D-N-methylalanine | Dnmala |
| D-N-methylarginine | Dnmarg |
| D-N-methylasparagine | Dnmasn |
| D-N-methylaspartate | Dnmasp |
| D-N-methylcysteine | Dnmcys |
| D-N-methylglutamine | Dnmgln |
| D-N-methylglutamate | Dnmglu |
| D-N-methylhistidine | Dnmhis |
| D-N-methylisoleucine | Dnmile |
| D-N-methylleucine | Dnmleu |
| D-N-methyllysine | Dnmlys |
| N-methylcyclohexylalanine | Nmchexa |
| D-N-methylornithine | Dnmorn |
| N-methylglycine | Nala |
| N-methylaminoisobutyrate | Nmaib |
| N-(1-methylpropyl)glycine | Nile |
| N-(2-methylpropyl)glycine | Nleu |
| D-N-methyltryptophan | Dnmtrp |
| D-N-methyltyrosine | Dnmtyr |
| D-N-methylvaline | Dnmval |
| γ-aminobutyric acid | Gabu |
| L-t-butylglycine | Tbug |
| L-ethylglycine | Etg |
| L-homophenylalanine | Hphe |
| L-α-methylarginine | Marg |
| L-α-methylaspartate | Masp |
| L-α-methylcysteine | Mcys |
| L-α-methylglutamine | Mgln |
| L-α-methylhistidine | Mhis |
| L-α-methylisoleucine | Mile |
| L-α-methylleucine | Mleu |
| L-α-methylmethionine | Mmet |
| L-α-methylnorvaline | Mnva |
| L-α-methylphenylalanine | Mphe |
| L-α-methylserine | Mser |
| L-α-methyltryptophan | Mtrp |
| L-α-methylvaline | Mval |
| N-(N-(2,2-diphenylethyl) carbamylmethyl)glycine | Nnbhm |
| 1-carboxy-1-(2,2-diphenyl-ethylamino)cyclopropane | Nmbc |
| L-N-methylalanine | Nmala |
| L-N-methylarginine | Nmarg |
| L-N-methylasparagine | Nmasn |
| L-N-methylaspartic acid | Nmasp |
| L-N-methylcysteine | Nmcys |
| L-N-methylglutamine | Nmgln |
| L-N-methylglutamic acid | Nmglu |
| Chexa L-N-methylhistidine | Nmhis |
| L-N-methylisolleucine | Nmile |
| L-N-methylleucine | Nmleu |
| L-N-methyllysine | Nmlys |
| L-N-methylmethionine | Nmmet |
| L-N-methylnorleucine | Nmnle |
| L-N-methylnorvaline | Nmnva |
| L-N-methylornithine | Nmorn |
| L-N-methylphenylalanine | Nmphe |
| L-N-methylproline | Nmpro |
| L-N-methylserine | Nmser |
| L-N-methylthreonine | Nmthr |
| L-N-methyltryptophan | Nmtrp |
| L-N-methyltyrosine | Nmtyr |
| L-N-methylvaline | Nmval |
| L-N-methylethylglycine | Nmetg |
| L-N-methyl-t-butylglycine | Nmtbug |
| L-norleucine | Nle |
| L-norvaline | Nva |
| α-methyl-aminoisobutyrate | Maib |
| α-methyl-γ-aminobutyrate | Mgabu |
| α-methylcyclohexylalanine | Mchexa |
| α-methylcylcopentylalanine | Mcpen |
| α-methyl-α-napthylalanine | Manap |
| α-methylpenicillamine | Mpen |
| N-(4-aminobutyl)glycine | Nglu |
| N-(2-aminoethyl)glycine | Naeg |
| N-(3-aminopropyl)glycine | Norn |
| N-amino-α-methylbutyrate | Nmaabu |
| α-napthylalanine | Anap |
| N-benzylglycine | Nphe |
| N-(2-carbamylethyl)glycine | Ngln |
| N-(carbamylmethyl)glycine | Nasn |
| N-(2-carboxyethyl)glycine | Nglu |
| N-(carboxymethyl)glycine | Nasp |
| N-cyclobutylglycine | Ncbut |
| N-cycloheptylglycine | Nchep |
| N-cyclohexylglycine | Nchex |
| N-cyclodecylglycine | Ncdec |
| N-cylcododecylglycine | Ncdod |
| N-cyclooctylglycine | Ncoct |
| N-cyclopropylglycine | Ncpro |
| N-cycloundecylglycine | Ncund |
| N-(2,2-diphenylethyl)glycine | Nbhm |
| N-(3,3-diphenylpropyl)glycine | Nbhe |
| N-(3-guanidinopropyl)glycine | Narg |
| N-(1-hydroxyethyl)glycine | Nthr |
| N-(hydroxyethyl))glycine | Nser |
| N-(imidazolylethyl))glycine | Nhis |
| N-(3-indolylyethyl)glycine | Nhtrp |
| N-methyl-γ-aminobutyrate | Nmgabu |
| D-N-methylmethionine | Dnmmet |
| N-methylcyclopentylalanine | Nmcpen |
| D-N-methylphenylalanine | Dnmphe |
| D-N-methylproline | Dnmpro |
| D-N-methylserine | Dnmser |
| D-N-methylthreonine | Dnmthr |
| N-(1-methylethyl)glycine | Nval |
| N-methyla-napthylalanine | Nmanap |
| N-methylpenicillamine | Nmpen |
| N-(p-hydroxyphenyl)glycine | Nhtyr |
| N-(thiomethyl)glycine | Ncys |
| penicillamine | Pen |
| L-α-methylalanine | Mala |
| L-α-methylasparagine | Masn |
| L-α-methyl-t-butylglycine | Mtbug |
| L-methylethylglycine | Metg |
| L-α-methylglutamate | Mglu |
| L-α-methylhomophenylalanine | Mhphe |
| N-(2-methylthioethyl)glycine | Nmet |
| L-α-methyllysine | Mlys |
| L-α-methylnorleucine | Mnle |
| L-α-methylornithine | Morn |
| L-α-methylproline | Mpro |
| L-α-methylthreonine | Mthr |
| L-α-methyltyrosine | Mtyr |
| L-N-methylhomophenylalanine | Nmhphe |
| N-(N-(3,3-diphenylpropyl) carbamylmethyl)glycine | Nnbhe |

Crosslinkers can be used, for example, to stabilise 3-D conformations, using homo-bifunctional crosslinkers such as the bifunctional imido esters having $(CH_2)_n$ spacer groups with n=1 to n=6, glutaraldehyde, N-hydroxysuccinimide esters and hetero-bifunctional reagents which usually contain an amino-reactive moiety such as N-hydroxysuccinimide and another group specific-reactive moiety such as maleimido or dithio moiety (SH) or carbodiimide (COOH). In addition, peptides can be conformationally constrained by, for example, incorporation of $C_\alpha$ and $N_\alpha$-methylamino acids, introduction of double bonds between $_\alpha C$ and $_\beta C$ atoms of amino acids and the formation of cyclic peptides or analogues by introducing covalent bonds such as forming an amide bond between the N and C termini, between two side chains or between a side chain and the N or C terminus.

The present invention further contemplates chemical analogues of musculin capable of acting as antagonists or agonists of musculin or which can act as functional analogues of musculin. Chemical analogues may not necessarily be derived from musculin but may share certain conformational similarities. Alternatively, chemical analogues may be specifically designed to mimic certain physiochemical properties of musculin. Chemical analogues may be chemically synthesised or may be detected following, for example, natural product screening. Useful sources for screening for natural products include coral, reefs, sea beds, river beds, plants, microorganisms and aquatic and antarctic environments.

The identification of musculin permits the generation of a range of therapeutic molecules capable of modulating expression of musculin or modulating the activity of musculin.

Modulators contemplated by the present invention includes agonists and antagonists of musculin expression. Antagonists of musculin expression include antisense molecules, ribozymes and co-suppression molecules. Agonists include molecules which increase promoter activity or interfere with negative regulatory mechanisms. Agonists of musculin include molecules which overcome any negative regulatory mechanism. Antagonists of musculin include antibodies and inhibitor peptide fragments.

In accordance with the present invention, it is proposed that musculin functions as a regulatory-type molecule in myogenesis. Hereditary myogenic cancers can arise with a mutation in the wild-type gene. The present invention extends to the use of modulating levels of expression of musculin or musculin in the context of regulating myogenesis.

Accordingly, another embodiment of the present invention contemplates a method for modulating expression of musculin in a human, said method comprising contacting musculin with an effective amount of a modulator of musculin expression for a time and under conditions sufficient to up-regulate or down-regulate or otherwise modulate expression of musculin. For example, a nucleic acid molecule encoding musculin or a derivative thereof may be introduced into a cell to enhance the ability of that cell to survive, conversely, musculin antisense sequences such as oligonucleotides may be introduced to decrease the survival capacity of any cell expressing an endogenous musculin.

Another aspect of the present invention contemplates a method of modulating activity of musculin in a human, said method comprising administering to said human a modulating effective amount of a molecule for a time and under conditions sufficient to increase or decrease the activity of musculin. The molecule may be a proteinaceous molecule or a chemical entity and may also be a derivative of musculin or a receptor thereof or a chemical analogue or truncation mutant of musculin or a receptor thereof. The present invention extends to these methods being applied in non-human mammals.

Both increased and decreased musculin expression or musculin activity may be important depending on the condition to be treated.

Accordingly, the present invention contemplates a pharmaceutical composition comprising musculin or a derivative thereof or a modulator of musculin expression or musculin activity and one or more pharmaceutically acceptable carriers and/or diluents. These components are referred to herein as the "active ingredients".

The pharmaceutical forms suitable for injectable use include sterile aqueous solutions (where water soluble) and sterile powders for the extemporaneous preparation of sterile injectable solutions. It must be stable under the conditions of manufacture and storage and must be preserved against the contaminating action of microorganisms such as bacteria and fungi. The carrier can be a solvent or, for example, water, ethanol, polyol (for example, glycerol, propylene glycol and liquid polyethylene glycol, and the like) or suitable mixtures thereof as well as vegetable oils. The preventions of the action of microorganisms can be brought about by various antibacterial and antifungal agents, for example, parabens, chlorobutanol, phenol, sorbic acid, thirmersal and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. In the case of sterile powders for the preparation of sterile injectable solutions, the preferred methods of preparation are vacuum drying and the freeze-drying technique which yield a powder of the active ingredient plus any additional desired ingredient from previously sterile-filtered solution thereof.

When the active ingredients are suitably protected they may be orally administered, for example, with an inert diluent or with an assimilable edible carrier, or it may be enclosed in hard or soft shell gelatin capsule, or it may be compressed into tablets, or it may be incorporated directly with the food of the diet. For oral therapeutic administration, the active compound may be incorporated with excipients and used in the form of ingestible tablets, buccal tablets, troches, capsules, elixirs, suspensions, syrups, wafers, and the like. Such compositions and preparations should contain at least 1% by weight of active compound. The percentage of the compositions and preparations may, of course, be varied and may conveniently be between about 5 to about 80% of the weight of the unit. The amount of active compound in such therapeutically useful compositions in such that a suitable dosage will be obtained. Preferred compositions or preparations according to the present invention are prepared so that an oral dosage unit form contains between about 0.1 $\mu$g and 2000 mg of active ingredient.

The tablets, troches, pills, capsules and the like may also contain the components as listed hereafter: a binder such as gum, acacia, corn starch or gelatin; excipients such as dicalcium phosphate; a disintegrating agent such as corn starch, potato starch, alginic acid and the like; a lubricant such as magnesium stearate; and a sweetening agent such a sucrose, lactose or saccharin may be added or a flavouring agent such as peppermint, oil of wintergreen, or cherry flavouring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavouring such as cherry or orange flavour. Of course, any material used in preparing any dosage unit form should be pharmaceutically pure and substantially non-toxic in the amounts employed. In addition, the active compound(s) may be incorporated into sustained-release preparations and formulations.

Pharmaceutically acceptable carriers and/or diluents include any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, use thereof in the therapeutic compositions is contemplated. Supplementary active ingredients can also be incorporated into the compositions.

It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active material calculated to produce the desired therapeutic effect in association with the required pharmaceutical carrier. The specification for the novel dosage unit forms of the invention are dictated by and directly dependent on (a) the unique characteristics of the active material and the particular therapeutic effect to be achieved, and (b) the limitations inherent in the art of compounding such an active material for the treatment of disease in living subjects having a diseased condition in which bodily health is impaired.

The principal active ingredient is compounded for convenient and effective administration in effective amounts with a suitable pharmaceutically acceptable carrier in dosage unit form as hereinbefore disclosed. A unit dosage form can, for example, contain the principal active compound in amounts ranging from 0.5 $\mu$g to about 2000 mg. Expressed in proportions, the active compound is generally present in from about 0.5 $\mu$g to about 2000 mg/ml of carrier. In the case of compositions containing supplementary active ingredients, the dosages are determined by reference to the usual dose and manner of administration of the said ingredients. It is also convenient to represent the effective amounts of active ingredients as an amount per kg body weight. For example, the present invention encompasses effective amounts from about 0.005 $\mu$g/kg body weight to about 200 mg/kg body weight or from about 0.01 $\mu$g/kg body weight to about 20 mg/kg body weight or about 0.1 $\mu$g/kg body weight about 15 mg/kg body weight.

The pharmaceutical composition may also comprise genetic molecules such as a vector capable of transfecting target cells where the vector carries a nucleic acid molecule capable of modulating musculin expression or musculin activity. The vector may, for example, be a viral vector.

Still another aspect of the present invention is directed to antibodies to musculin and its derivatives. Such antibodies may be monoclonal or polyclonal and may be selected from naturally occurring antibodies to musculin or may be specifically raised to musculin or derivatives thereof. In the case of the latter, musculin or its derivatives may first need to be associated with a carrier molecule. The antibodies to musculin or its derivatives of the present invention are particularly useful as therapeutic or diagnostic agents.

For example, musculin and its derivatives can be used to screen for naturally occurring antibodies to musculin. These may occur, for example in some autoimmune diseases. Alternatively, specific antibodies can be used to screen for musculin. Techniques for such assays are well known in the art and include, for example, sandwich assays and ELISA. Knowledge of musculin levels may be important for diagnosis of myogenic disorders or a predisposition to developing myogenic disorders or for monitoring certain therapeutic protocols.

Antibodies to the musculin of the present invention may be monoclonal or polyclonal. Alternatively, fragments of antibodies may be used such as Fab fragments. Furthermore, the present invention extends to recombinant and synthetic antibodies and to antibody hybrids. A "synthetic antibody" is considered herein to include fragments and hybrids of antibodies. The antibodies of this aspect of the present invention are particularly useful for immunotherapy and may also be used as a diagnostic tool for assessing cell apoptosis or monitoring the program of a therapeutic regimum.

For example, specific antibodies can be used to screen for the musculin gene translation product proteins. The latter would be important, for example, as a means for screening for levels of musculin in a cell extract or other biological fluid or purifying the musculin gene translation product made by recombinant means from culture supernatant fluid. Techniques for the assays contemplated herein are known in the art and include, for example, sandwich assays and ELISA.

It is within the scope of this invention to include any second antibodies (monoclonal, polyclonal or fragments of antibodies or synthetic antibodies) directed to the first mentioned antibodies discussed above. Both the first a nd second antibodies may be used in detection assays or a first antibody may be used with a commercially available anti-immunoglobulin antibody. An antibody as contemplated herein includes any antibody specific to any region of musculin.

Both polyclonal and monoclonal antibodies are obtainable by immunization with the enzyme or protein and either type is utilizable for immunoassays. The methods of obtaining both types of sera are well known in the art. Polyclonal sera are less preferred but are relatively easily prepared by injection of a suitable laboratory animal with an effective amount of the tumour suppression gene translation product, or antigenic parts thereof, collecting serum from the animal, and isolating specific sera by any of the known immunoadsorbent techniques. Although antibodies produced by this method are utilizable in virtually any type of immunoassay, they are generally less favoured because of the potential heterogeneity of the product.

The use of monoclonal antibodies in an immunoassay is particularly preferred because of the ability to produce them in large quantities and the homogeneity of the product. The preparation of hybridoma cell lines for monoclonal antibody production derived by fusing an immortal cell line and lymphocytes sensitized against the immunogenic preparation can be done by techniques which are well known to those who are skilled in the art (see, for example references 8, 9, 10).

Another aspect of the present invention contemplates a method for detecting musculin in a biological sample from a subject said method comprising contacting said biological sample with an antibody specific for musculin or its derivatives or homologues for a time and under conditions sufficient for an antibody-musculin complex to form, and then detecting said complex.

The presence of musculin may be accomplished in a number of ways such as by Western blotting and ELISA procedures. A wide range of immunoassay techniques are available as can be seen by reference to U.S. Pat. Nos. 4,016,043, 4,424,279 and 4,018,653. These include both single-site and two-site or "sandwich" assays of the non-competitive types, as well as in the traditional competitive binding assays. These assays also include direct binding of a labelled antibody to a target.

Sandwich assays are among the most useful and commonly used assays and are favoured for use in the present invention. A number of variations of the sandwich assay technique exist and all are intended to be encompassed by the present invention. Briefly, in a typical forward assay, an unlabelled antibody is immobilized to a solid substrate and the sample to be tested brought into contact with the bound molecule. After a suitable period of incubation, for a period of time sufficient to allow formation of an antibody-antigen complex, a second antibody specific to the antigen, labelled with a reporter molecule capable of producing a detectable signal is then added and incubated, allowing time sufficient for the formation of another complex of antibody-antigen-labelled antibody. Any unreacted material is washed away and the presence of the antigen is determined by observation of a signal produced by the reporter molecule. The results may either be qualitative, by simple observation of the visible signal, or may be quantitated by comparing with a control sample containing known amounts of hapten. Variations on the forward assay include a simultaneous assay, in which both sample and labelled antibody are added simultaneously to the bound antibody. These techniques are well known to those skilled in the art, including any minor variations as will be readily apparent. In accordance with the present invention the sample is one which might contain musculin including cell extract, tissue biopsy or possibly serum, saliva, mucosal secretions, lymph, tissue fluid and gastrointestinal fluid. The sample is, therefore, generally a biological sample comprising biological fluid but also extends to fermentation fluid and supernatant fluid such as from a cell culture.

In the typical forward sandwich assay, a first antibody having specificity for musculin or antigenic parts thereof, is either covalently or passively bound to a solid surface. The solid surface is typically glass or a polymer, the most commonly used polymers being cellulose, polyacrylamide, nylon, polystyrene, polyvinyl chloride or polypropylene. The solid supports may be in the form of tubes, beads, discs of microplates, or any other surface suitable for conducting an immunoassay. The binding processes are well-known in the art and generally consist of cross-linking covalently binding or physically adsorbing, the polymer-antibody complex is washed in preparation for the test sample. An aliquot of the sample to be tested is then added to the solid phase complex and incubated for a period of time sufficient (e.g. 240 minutes or overnight if more convenient) and under suitable conditions (e.g. from room temperature to 37° C.) to allow binding of any subunit present in the antibody. Following the incubation period, the solid phase complex is washed and dried and incubated with a second antibody which is specific for a portion of the antigen (i.e. musculin). The second antibody is linked to a reporter molecule which is used to indicate the binding of the second antibody to musculin.

An alternative method involves immobilizing the target molecules in the biological sample and then exposing the immobilized target to specific antibody which may or may not be labelled with a reporter molecule. Depending on the amount of target and the strength of the reporter molecule signal, a bound target may be detectable by direct labelling with the antibody. Alternatively, a second labelled antibody, specific to the first antibody is exposed to the target-first antibody complex to form a target-first antibody-second antibody tertiary complex. The complex is detected by the signal emitted by the reporter molecule.

By "reporter molecule" as used in the present specification, is meant a molecule which, by its chemical nature, provides an analytically identifiable signal which allows the detection of antigen-bound antibody. Detection may be either qualitative or quantitative. The most commonly used reporter molecules in this type of assay are either enzymes, fluorophores or radionuclide containing molecules (i.e. radioisotopes) and chemiluminescent molecules.

In the case of an enzyme immunoassay, an enzyme is conjugated to the second antibody, such as via glutaraldehyde or periodate amongst other means. As will be readily recognized, however, a wide variety of different conjugation techniques exist, which are readily available to the skilled artisan. Commonly used enzymes include horseradish peroxidase, glucose oxidase, beta-galactosidase and alkaline phosphatase, amongst others. The substrates to be used with the specific enzymes are generally chosen for the production, upon hydrolysis by the corresponding enzyme, of a detectable colour change. It is also possible to employ fluorogenic substrates, which yield a fluorescent product rather than the chromogenic substrates noted above. In all cases, the enzyme-labelled antibody is added to the first antibody-antigen complex, allowed to bind, and then the excess reagent is washed away. A solution containing the appropriate substrate is then added to the complex of antibody-antigen-antibody. The substrate will react with the enzyme linked to the second antibody, giving a qualitative visual signal, which may be further quantitated, usually spectrophotometrically, to give an indication of the amount of antigen which was present in the sample. The term "reporter molecule" also extends to use of cell agglutination or inhibition of agglutination such as red blood cells on latex beads, and the like.

Alternately; fluorescent compounds, such as fluorescein and rhodamine, may be chemically coupled to antibodies without altering their binding capacity. When activated by illumination with light of a particular wavelength, the fluorochrome-labelled antibody adsorbs the light energy, inducing a state of excitability in the molecule, followed by emission of the light at a characteristic colour visually detectable with a light microscope. As in the EIA, the fluorescent labelled antibody is allowed to bind to the first antibody-hapten complex. After washing off the unbound reagent, the remaining tertiary complex is then exposed to light of the appropriate wavelength and the fluorescence observed indicates the presence of the antigen of interest. Immunofluorescene and EIA techniques are both very well established in the art. Other reporter molecules, such as radioisotope, chemiluminescent or bioluminescent molecules, may also be employed.

The present invention also contemplates genetic assays such as involving PCR analysis to detect musculin or its derivatives. Alternative methods or methods used in conjunction include direct nucleotide sequencing or mutation scanning such as single stranded conformation polymorphoms analysis (SSCP) as specific oligonucleotide hybridisation, as methods such as direct protein truncation tests (see, for example, Van der Luut et al, [11]).

Although the present invention does not extend to ABF-1, genetic sequences from, complementary to or capable of hybridizing with the ABF-1 gene or its mRNA, may be useful as antagonists of musculin gene expression. A human gene corresponding to musculin was identified by the inventors and this is shown in <400>3 (SEQ ID NO: 3) together with its corresponding amino acid sequence (<400>4) (SEQ ID NO: 4). Nucleotide sequences from this gene may also be used as antisense molecules, sense molecules, probes or primers for murine musculin or musculin genes from other species.

The present invention is further described by the following non-limiting Examples.

EXAMPLE 1

The genetic sequence database of The National Center for Biotechnology Information (Genbank) was searched with a bHLH search motif using the TBLASTN programme (27). The search motif is $NXXERXRX_7F/L-X_{8-30}-KXXI/V/TLXXAXXY$ wherein X is any amino acid. The EST YX52E05.R1 was used as a probe to screen a human placental cDNA library, with additional clones obtained from human bone marrow, peripheral blood and HL60 libraries. Murine musculin cDNA clones were obtained from a 11 dpc embryo cDNA library.

EXAMPLE 2

Northern blot analysis and RNase protection analysis of polyA+ RNA from murine tissues and cell lines were performed as described (21, 22). Activated Bcells were prepared by incubation of splenocytes at $5 \times 10^5$/ml with 20 µg/ml E. coli LPS, (Difco) for three days followed by anti-Thyl T-cell depletion. Protocols for in situ hybridisation of embryos and paraffin-embedded sections were as described (23, 24), except that embryos and sections were treated with 20 µg/ml of proteinase K (Boehringer).

EXAMPLE 3

This example presents a novel bHLH gene called herein "musculin", based on its expression in embryonic skeletal muscle.

Using the strategy described herein (Example 1), a human EST (YX52E05.R1) with the potential to encode a novel bHLH protein was identified and used to screen human cDNA libraries. A cDNA molecule similar in sequence to the human gene ABF-1 (5), was cloned and characterized (see nucleotide sequence in <400>3 (SEQ ID NO: 3)), then used to screen for murine cDNAs. The murine musculin cDNA encoded an amino acid sequence set forth in FIG 1A and in <400>2 (SEQ ID NO: 2) (FIG. 1A).

Northern analysis of polyA+ mRNA extracted from a range of adult murine tissues, including lymphoid organs and skeletal muscle, failed to detect musculin expression, although a single transcript of 1.8 kb was observed in RNA from 14.5 days post coitum (dpc) embryos. However, RNase protection analysis detected low expression in spleen and a range of other adult tissues (FIG. 1C). Analysis of polyA+ RNA from 42 cell lines representing numerous hemopoietic lineages, as well as activated murine splenic B-cells, failed to detect musculin expression. This pattern differs from that of human ABF-1, which is highly expressed in SAC-activated B-cells and adult lymphoid tissues (5).

Figure 2:
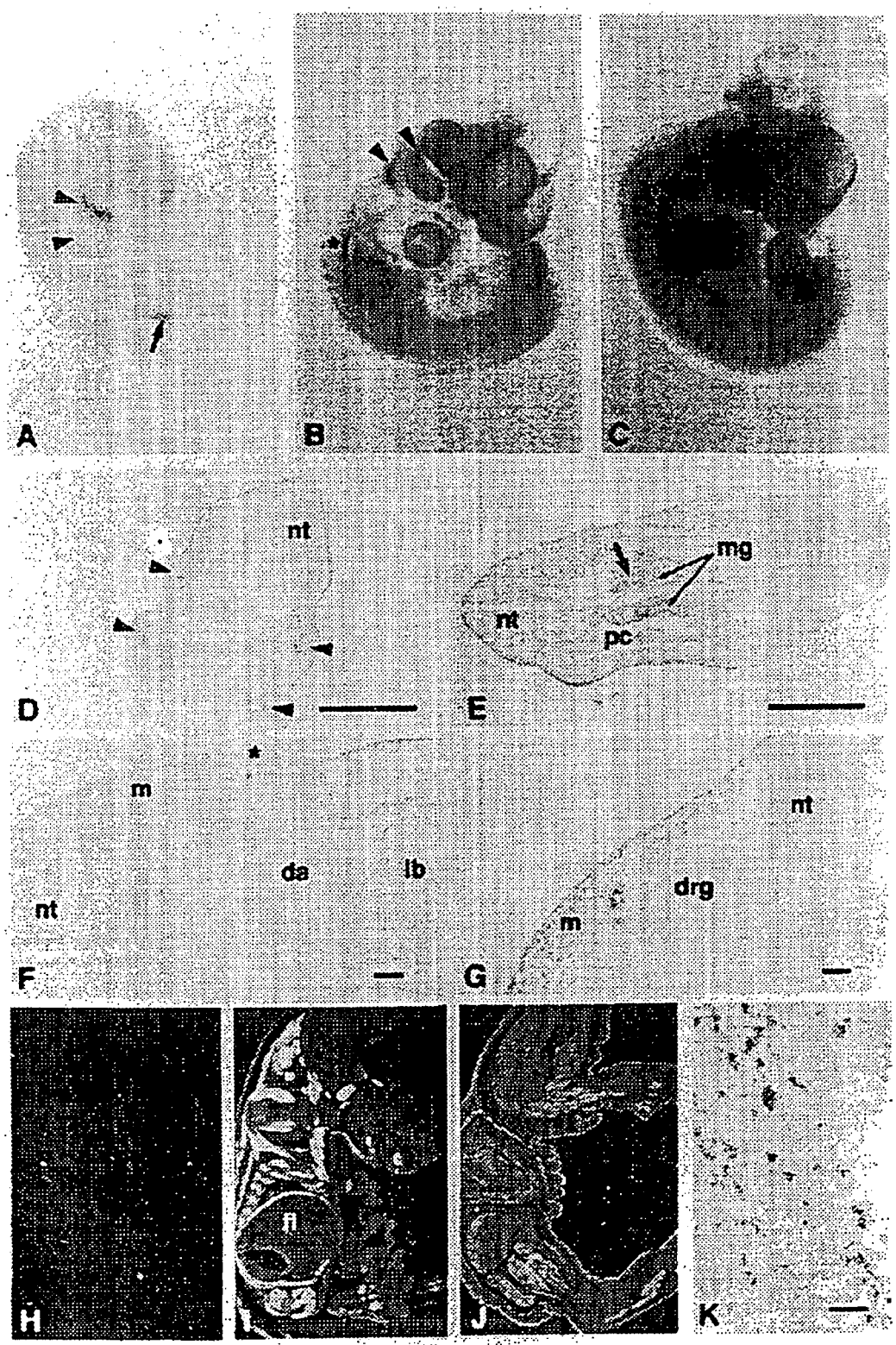
FIGS. 2A–2K are a photographic representation of expression of musculin in the developing murine embryo. (A–C) expression of musculin in (A) 9.5 days post coitus (dpc), (B) 10.5 dpc (C) 11.5 dpc embryos, detected by in situ hybridization with digoxigenin-labelled musculin riboprobes. Arrow: musculin expression in mesoderm adjacent to foregut and midgut endoderm. Arrow heads: musculin expression in the branchial arches. (D) traverse section of 9.5 dpc embryo after in situ hybridization with a musculin riboprobe. Arrow: region of mesoderm indicated in (A); mg, midgut; nt, neural tube, pc, peritoneal cavity. (E) Transverse section of myotome of 11.5 dpc embryo after in situ hybridization with a musculin riboprobe. Expression is seen in the epaxial dermomyotomal lip, drg, dorsal root ganglion; m, myotome; nt, neural tube. (F, G) Sagittal section of a 14.5 dpc embryo, hybridized with sense control (F) and antisense (G) {$^{32}$P}-radiolabelled musculin riboprobes. fl, fetal liver. (H) Lateral sagittal section of 18.5 dpc embryo, probed with an antisense musculin riboprobe. The signal in dermis was also seen in sections hybridized with a sense probe and is an artefact. (I) Section of latissimus dorsi muscle in a 14.5 dpc embryo showing localization of musculin expression in a subset of muscle fibres.

Musculin expression in 7.5–11.5 dpc embryos was analysed by whole mount in situ hybridisation. Transcripts were first detected at 9.5 dpc in myoblasts located centrally within the first and second branchial arches (FIGS. 2A, B). At E10.5, expression was also observed in the myotomal compartment of rostral somites (FIG. 2B), and by 11.5 dpc in myotomes along the antero-posterior axis, as well as in developing muscles of forelimbs and hindlimbs (FIG. 2C). Within the myotome, expression was strongest in the epaxial dermamyotomal lip (FIG. 2E). The only non-myogenic site of musculin expression was located in a region of splanchnic mesoderm at 9.5 dpc located close to the foregut/midgut junction (FIGS. 2A, D). This was transient and no longer detected by 10 dpc.

In situ hybridisation to sections of 12.5, 14.5 and 18.5 dpc embryos using ($^{33}$P)-radiolabelled musculin riboprobes revealed expression was confined to the skeletal muscle lineage (FIGS. 2F–I). All skeletal muscles of the embryo expressed the gene, including those of the head, neck, trunk, limbs, and diaphragm (FIG. 2F–H). Cardiac and smooth muscles were negative. RNase protection revealed peak expression in embryonic limbs around 15 dpc, although expression in neonatal limbs was still robust. Higher power examination of sections revealed that musculin expression was localised to only a subset of muscle fibres from at least as early as 12.5 dpc (FIG. 2I).

Although expressed almost exclusively in embryonic skeletal muscle, musculin does not contain the alanine/threonine dipeptide which is found in the basic region of myoD-related bHLH factors (FIG. 1B) and which plays a critical role in activation of skeletal myogenesis through a direct interaction with the MADS box factor Mef2 (25). The myotome, from which most skeletal muscles derive, is a complex structure what may be assembled from cell populations arising in different regions of the dermamyotome (26).

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

BIBLIOGRAPHY

1. Jan and Jan Cell 75: 827–830, 1993.
2. Murre et al. biochim. Biophysica Acta 1218: 129–135, 1994.
3. Murre et al. Cell 56: 777–783, 1989.
4. Voronova and Baltimore Proc. Natl. Acad. Sci. USA 87: 4722–4726, 1990.
5. Massari et al. Mol. Cell. Biol. 18: 3130–3139, 1998.
6. Akajawa et al. J. Biol. Chem. 270: 8730–8736, 1995.
7. Begley et al. Proc. Natl. Acad. Sci. USA 89: 38–42, 1992.
8. Doullard and Hoffman "Basic facts about hybridomas" in Compendium of Immunology vol. II ed. by Schwartz (1981).
9. Kohler & Milstein Nature Nature 256: 495–499, 1975.
10. Kohler & Milstein Euro. J. Immunol. 6: 511–519, 1996.
11. van de Luut et al. Genomics 20: 1–4, 1994.
12. Burgess et al. Dev. Biol. 168: 296–306, 1995.
13. Cserjesi et al. Development 121: 1099–1510, 1995.

14. Davis et al. *Cell* 51: 957–1000, 1987.
15. Edmondson and Olson *Genes. Devel.* 3: 628–640, 1989.
16. Georgias et al. *Mech. Dev.* 69: 115–124, 1997.
17. Srivastava et al. *Science* 270: 1995–1999, 1995.
18. Wolf et al. *Dev. Biol.* 143: 363–373, 1991.
19. Marmur and Doty *J. Mol. Biol.* 5: 109, 1962.
20. Bonner et al. *J. Mol. Biol.* 81: 123, 1973.
21. Robb et al. *J. Biol. Chem.* 271: 13754–13761, 1996.
22. Robb et al. *Nature Med.* 4: 303–308, 1998.
23. Lyons et al. *Genes. Deve.* 9: 1654–1666, 1995.
24. Wilkinson *Whole mount in situ hybridization of vertebrate embryos.* In situ hybridisation. A practical approach. Wilkinson (ed.) Oxford University Press, Oxford, UK.
25. Molkentin er al. *Cell* 83: 1125–1136, 1995.
26. Tajbakhsh and Sporle *Cell* 92: 9–16, 1998.
27. Altschul et al. *J. Mol. Biol.* 215: 403–410, 1990.

What is claimed is:

1. An isolated nucleic acid encoding murine musculin comprising the amino acid sequence of SEQ ID NO:2.

2. The isolated nucleic acid of claim 1 comprising a nucleotide sequence of SEQ ID NO:1.

3. A genetic construct comprising the nucleic acid of any one of claims 1-2.

4. The genetic construct of claim 3, wherein the construct is an expression vector capable of expressing said nucleic acid in a prokaryotic cell.

5. The genetic construct of claim 3, wherein the construct is an expression vector capable of expressing said nucleic acid in a eukaryotic cell.

* * * * *

SEQUENCE LISTING

```
<160> NUMBER OF SEQ ID NOS: 4

<210> SEQ ID NO 1
<211> LENGTH: 1718
<212> TYPE: DNA
<213> ORGANISM: Mouse
<220> FEATURE:
<221> NAME/KEY: CDS
<222> LOCATION: (219)...(821)

<400> SEQUENCE: 1
aagttcagca gagccctggg ctacagggtc agcagcagat cgcgcccact ccaggcgccc        60
agctcacagg ggagcctcag tgcggaggca agccctggtc tctggtcctc ccctgggctc       120
tcccacaccc catcctctgt cagagagaag aagcagaga aagcgagact ggccggggag        180
gagaaaggcg ggcgcgcgtg ggcgccgggg aataggcg atg tcc acc ggc tcg gtg       236
                                           Met Ser Thr Gly Ser Val
                                             1               5 agt gac ccc gaa gac tcg gag atg agg ggg ctg cag agg gtc tac ccg         284
Ser Asp Pro Glu Asp Ser Glu Met Arg Gly Leu Gln Arg Val Tyr Pro
             10                  15                  20 gcc ccg gcc tcc aag agg ccg ccc ctg ctc cgc atg gag cgc ggt tac         332
Ala Pro Ala Ser Lys Arg Pro Pro Leu Leu Arg Met Glu Arg Gly Tyr
         25                  30                  35 ggc tcg ccc agc gac att tct tct gcg gaa gag gag gac ggt gaa gag         380
Gly Ser Pro Ser Asp Ile Ser Ser Ala Glu Glu Glu Asp Gly Glu Glu
     40                  45                  50 gag ccc ggc tcc ctg gga gcc gcg gga gga tgc aag agg aag cgg ctc         428
Glu Pro Gly Ser Leu Gly Ala Ala Gly Gly Cys Lys Arg Lys Arg Leu
 55                  60                  65                  70 cgt ggg gct gac gct ggc ggc gca ggt ggc cgc gca ggc ggt gcg ggg         476
Arg Gly Ala Asp Ala Gly Gly Ala Gly Gly Arg Ala Gly Gly Ala Gly
                 75                  80                  85 aaa aag ccg ctc ccg cct aag ggc tcg gcc gca gag tgc aag cag tcg         524
Lys Lys Pro Leu Pro Pro Lys Gly Ser Ala Ala Glu Cys Lys Gln Ser
             90                  95                 100 cag cgg aat gcg gcc aac gcc cgc gaa cgc gcc cgg atg cgc gtg ctg         572
Gln Arg Asn Ala Ala Asn Ala Arg Glu Arg Ala Arg Met Arg Val Leu
         105                 110                 115 agc aaa gcc ttc tcc aga ctg aag acc agc ctg ccc tgg gtg ccg ccc         620
Ser Lys Ala Phe Ser Arg Leu Lys Thr Ser Leu Pro Trp Val Pro Pro
     120                 125                 130 gac acc aag ctt tcc aaa ctg gac acg ctg cgc ctg gct tcc agc tac         668
Asp Thr Lys Leu Ser Lys Leu Asp Thr Leu Arg Leu Ala Ser Ser Tyr
135                 140                 145                 150 atc gcg cac ctg cgc cag ctg ctg cag gag gac cgc tac gag gac agc         716
Ile Ala His Leu Arg Gln Leu Leu Gln Glu Asp Arg Tyr Glu Asp Ser
                 155                 160                 165 tat gtg cac cct gtg aac ctg acg tgg cca ttc gtg gtc tct gga cgc         764
Tyr Val His Pro Val Asn Leu Thr Trp Pro Phe Val Val Ser Gly Arg
             170                 175                 180
```

```
cca gac tct gac agc aaa gac gtt tct gca gcc aac agg ctt tgt gga      812
Pro Asp Ser Asp Ser Lys Asp Val Ser Ala Ala Asn Arg Leu Cys Gly
        185                 190                 195 act tcc gct tagagggaca ggacagttag atggattgtg gtaaacgcaa               861
Thr Ser Ala
    200 aggactgggc caaggaagtc ccactggatt ctggaccttc tcctttccct gggcctgtga     921
acaagacagg agacaagtgt tgtttgccct cctggagcgc agtggccat gggtgcccca      981
aatcagtgca aacttctgta accaaagaaa gcccagtttc aggggaagaa tacgtggacc    1041
aggtaaaaac ctagggcttt agctctgatc acaaccccct gcctgctatc tgagtccagt    1101
gcagaaacgg gttggttttg aagctaatct tgattgcctt gtggttgatg caaggtcct     1161
gcacagccag gtccttctgt gaccgtggat gagagctgtt tcccagcact agaaagaagg    1221
ccggcattag agctcttcgg gggcctgtca ctaagggcag tgttgctaca gacagtggca    1281
tactcttcct gggcaggaca tgttgagatg gagacattaa ctccaggtgc tggttttgct    1341
cgaaatctct gcagactggg gttcatttcc tgagttccct cctctgttta atcagtgttg    1401
ggtctccatt cagtgagtgc agcttgttta tggggtctca gctccttccc acccacactg    1461
tcccctattt ggggacatgt gcttcacccc tctaattgtc tcaccctgcc acagcatagc    1521
cttctgtggg gttcctggtc tttcagggat gtactattct tcctggtcca aggactgtgt    1581
gtggtgggtg gctggggcta gggctggtct ctattatact ggtttctacc cagtacatgg    1641
tgcttactgg tcctggcaat gctgcactat catggtaact aacatatgta aataaattta    1701
ttttttatgg acaaaaa                                                    1718
```

<210> SEQ ID NO 2
<211> LENGTH: 201
<212> TYPE: PRT
<213> ORGANISM: Mouse

<400> SEQUENCE: 2

```
Met Ser Thr Gly Ser Val Ser Asp Pro Glu Asp Ser Glu Met Arg Gly
 1               5                   10                  15

Leu Gln Arg Val Tyr Pro Ala Pro Ala Ser Lys Arg Pro Pro Leu Leu
                20                  25                  30

Arg Met Glu Arg Gly Tyr Gly Ser Pro Ser Asp Ile Ser Ser Ala Glu
            35                  40                  45

Glu Glu Asp Gly Glu Glu Glu Pro Gly Ser Leu Gly Ala Ala Gly Gly
        50                  55                  60

Cys Lys Arg Lys Arg Leu Arg Gly Ala Asp Ala Gly Gly Ala Gly Gly
65                  70                  75                  80

Arg Ala Gly Gly Ala Gly Lys Lys Pro Leu Pro Pro Lys Gly Ser Ala
                85                  90                  95

Ala Glu Cys Lys Gln Ser Gln Arg Asn Ala Ala Asn Ala Arg Glu Arg
            100                 105                 110

Ala Arg Met Arg Val Leu Ser Lys Ala Phe Ser Arg Leu Lys Thr Ser
        115                 120                 125

Leu Pro Trp Val Pro Pro Asp Thr Lys Leu Ser Lys Leu Asp Thr Leu
    130                 135                 140

Arg Leu Ala Ser Ser Tyr Ile Ala His Leu Arg Gln Leu Leu Gln Glu
145                 150                 155                 160

Asp Arg Tyr Glu Asp Ser Tyr Val His Pro Val Asn Leu Thr Trp Pro
                165                 170                 175
```

```
Phe Val Val Ser Gly Arg Pro Asp Ser Asp Ser Lys Asp Val Ser Ala
            180                 185                 190

Ala Asn Arg Leu Cys Gly Thr Ser Ala
            195                 200

<210> SEQ ID NO 3
<211> LENGTH: 1716
<212> TYPE: DNA
<213> ORGANISM: Homo sapiens
<220> FEATURE:
<221> NAME/KEY: CDS
<222> LOCATION: (2)...(604)

<400> SEQUENCE: 3 g gtg agt gat ccg gag gag atg gag ctt cgg ggg ctg cag cgg gag tac      49
  Val Ser Asp Pro Glu Glu Met Glu Leu Arg Gly Leu Gln Arg Glu Tyr
   1               5                  10                  15 ccg gtc ccc gcc tcc aag agg ccg ccc ctc cgc ggc gta gag cgc agc        97
Pro Val Pro Ala Ser Lys Arg Pro Pro Leu Arg Gly Val Glu Arg Ser
             20                  25                  30 tac gcc tcg ccc agt gac aac tcg tcg gca gag gag gag gac ccc gac        145
Tyr Ala Ser Pro Ser Asp Asn Ser Ser Ala Glu Glu Glu Asp Pro Asp
         35                  40                  45 ggc gag gag gag cgc tgc gct ctg ggc aca gcc ggc agc gcg gaa ggc        193
Gly Glu Glu Glu Arg Cys Ala Leu Gly Thr Ala Gly Ser Ala Glu Gly
 50                  55                  60 tgc aag agg aag cgg ccc cgc ggg gct ggg ggc ggc gca ggt ggt            241
Cys Lys Arg Lys Arg Pro Arg Gly Ala Gly Gly Gly Ala Gly Gly
 65                  70                  75                  80 agc gcg ggc ggt ggt ggc aag aag ccc ctc ccg gcc aag ggc tca gcc        289
Ser Ala Gly Gly Gly Lys Lys Pro Leu Pro Ala Lys Gly Ser Ala
                 85                  90                  95 gca gag tgc aag cag tcg cag cgg aac gcg gcc aac gcc cgt gag cgt        337
Ala Glu Cys Lys Gln Ser Gln Arg Asn Ala Ala Asn Ala Arg Glu Arg
             100                 105                 110 gcc cgg atg cgc gtg ctg agc aaa gcc ttc tcc agg ctc aag acc agc        385
Ala Arg Met Arg Val Leu Ser Lys Ala Phe Ser Arg Leu Lys Thr Ser
         115                 120                 125 ctg ccc tgg gtg ccc ccc gac act aag ctc tcc aag ctg gac acg ctc        433
Leu Pro Trp Val Pro Pro Asp Thr Lys Leu Ser Lys Leu Asp Thr Leu
 130                 135                 140 cgg ctg gct tcc agt tac atc gct cac ctg cgg cag ctg ttg cag gag        481
Arg Leu Ala Ser Ser Tyr Ile Ala His Leu Arg Gln Leu Leu Gln Glu
145                 150                 155                 160 gac cgc tat gag aac ggc tac gtg cac cca gtg aac ctg aca tgg cca        529
Asp Arg Tyr Glu Asn Gly Tyr Val His Pro Val Asn Leu Thr Trp Pro
                 165                 170                 175 ttc gtg gtc tcg gga aga ccg gac tct gac acc aaa gaa gtt tcc gca        577
Phe Val Val Ser Gly Arg Pro Asp Ser Asp Thr Lys Glu Val Ser Ala
             180                 185                 190 gcc aac aga cta tgt gga acc acc gct taaatcggac tggaactcac             624
Ala Asn Arg Leu Cys Gly Thr Thr Ala
         195                 200 ttgatgggat tattcgttaa atgcgagtgt ttggggggcca cggagagaag ggagagctcg     684
tgagatggga agaagtttcc gctggattct ccttgaccct tccccttttcc ctggaactgt    744 gatcgtgaca ggtggcgggt gtggctgtca ctgcacagcg cccacggcta cagctgcgcc    804
ggatctgggc gaccacgttt tgcctctcca aaaagagctt cctttcgtga cgagacgcgg    864
acgcaggtcc accctcgggc cctagctctg tagactaact ctcggctgct gccccagccc    924
```

-continued

| | |
|---|---|
| gcgccagaca gcccacggat ccgttctcag cggagccaga ttcatcgcac acgtgcggga | 984 |
| cggttccaca cagccccggc cttcgcggt gacacaatgg ttagggaacg gttagaacgc | 1044 |
| gctctacatc cgctttaaag acagaggtct agacgtgaga tccgcgtcgg gacagggttt | 1104 |
| taagtgacaa agaagggcga gtggcttctc tgggccgggt tcgtactcca gcacagcgcc | 1164 |
| cttctaacgg gcgggaggaa ggccgctgct cgcagggcta ggtggagaca cacttcccag | 1224 |
| atcaccgcag gcgggtttta cccggagagc tctaggccgt tcggcctccc tgccgggtgg | 1284 |
| cttcttcaat cccgtctcct tcccaagctc ccggcttttt ctaatcaggc aggcgtctgt | 1344 |
| caaccctctc cacttctggg ctgaagcctc cccaagcccc gtgcgccaac ctgtgtgggg | 1404 |
| tcttcttcgg gcctcccttt ccgccccgct cctgctccta cctgcagcac ccccagctcc | 1464 |
| gactccagac tctctgcatc aggtctcccc actccacgct ccgggcgccc caactccaac | 1524 |
| accacgtcct gccgcgcagg ttcttccccg cgcggaggag cgcgcagggt gggcggctta | 1584 |
| ccatagcaag tgatcctgcg atagggaacg cgcccttgcc ccgaggctgc actaccacag | 1644 |
| gaaataacat atgtaaataa atttattttt ttatgaataa taaaacgcgc tgtaaaaacc | 1704 |
| gtggacggaa aa | 1716 |

<210> SEQ ID NO 4
<211> LENGTH: 201
<212> TYPE: PRT
<213> ORGANISM: Homo sapiens

<400> SEQUENCE: 4

Val Ser Asp Pro Glu Glu Met Glu Leu Arg Gly Leu Gln Arg Glu Tyr
1               5                   10                  15

Pro Val Pro Ala Ser Lys Arg Pro Leu Arg Gly Val Glu Arg Ser
        20                  25                  30

Tyr Ala Ser Pro Ser Asp Asn Ser Ala Glu Glu Asp Pro Asp
    35                  40                  45

Gly Glu Glu Arg Cys Ala Leu Gly Thr Ala Gly Ser Ala Glu Gly
    50                  55                  60

Cys Lys Arg Lys Arg Pro Arg Gly Ala Gly Gly Gly Ala Gly Gly
65                  70                  75                  80

Ser Ala Gly Gly Gly Lys Lys Pro Leu Pro Ala Lys Gly Ser Ala
            85                  90                  95

Ala Glu Cys Lys Gln Ser Gln Arg Asn Ala Ala Asn Ala Arg Glu Arg
                100                 105                 110

Ala Arg Met Arg Val Leu Ser Lys Ala Phe Ser Arg Leu Lys Thr Ser
            115                 120                 125

Leu Pro Trp Val Pro Pro Asp Thr Lys Leu Ser Lys Leu Asp Thr Leu
    130                 135                 140

Arg Leu Ala Ser Ser Tyr Ile Ala His Leu Arg Gln Leu Leu Gln Glu
145                 150                 155                 160

Asp Arg Tyr Glu Asn Gly Tyr Val His Pro Val Asn Leu Thr Trp Pro
                165                 170                 175

-continued

```
Phe Val Val Ser Gly Arg Pro Asp Ser Asp Thr Lys Glu Val Ser Ala
            180                 185                 190

Ala Asn Arg Leu Cys Gly Thr Thr Ala
        195                 200
```